Figure 1:
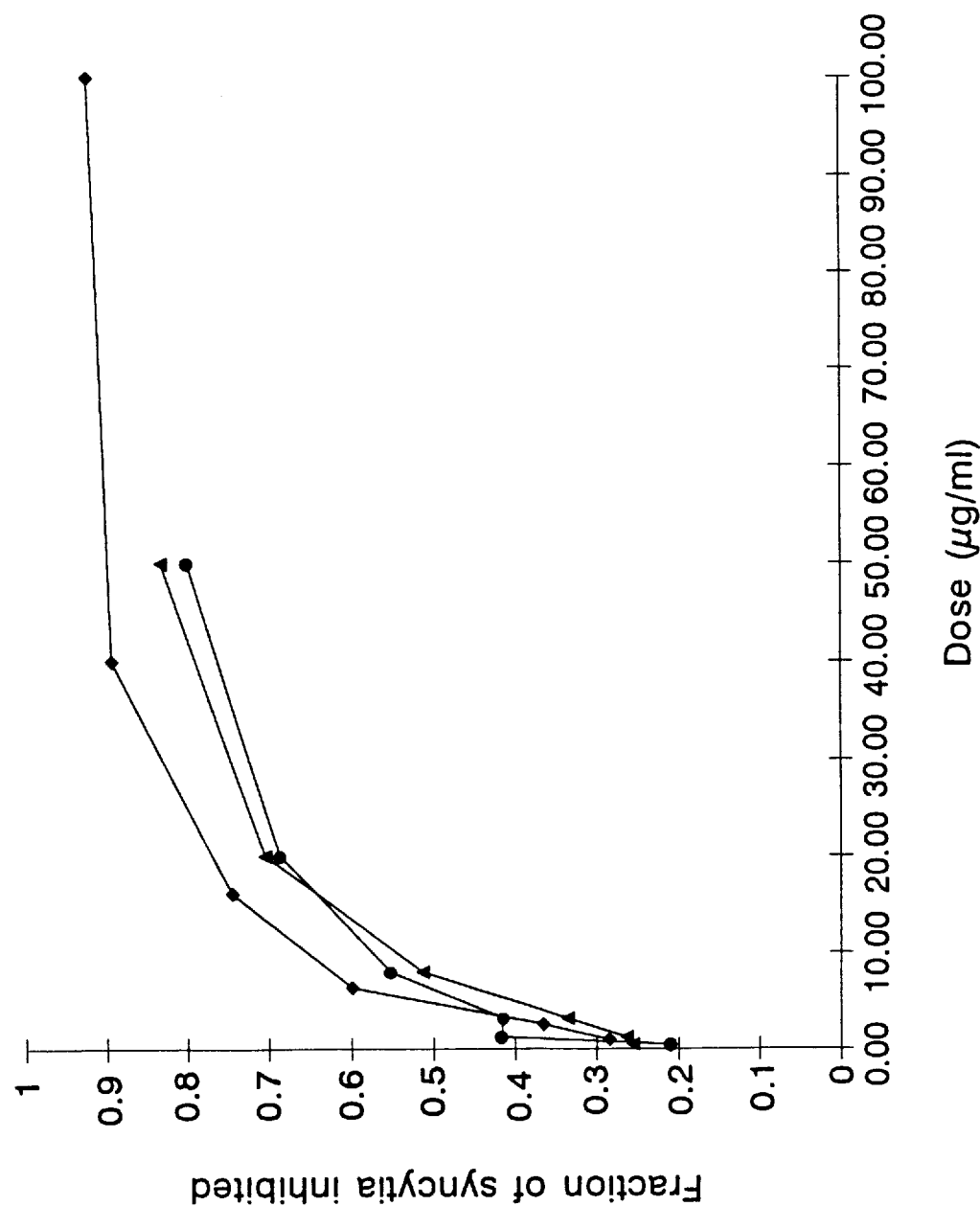

United States Patent [19]
Allaway et al.

[11] Patent Number: 5,817,767
[45] Date of Patent: Oct. 6, 1998

[54] SYNERGISTIC COMPOSITION OF CD4-BASED PROTEIN AND ANTI-HIV-1 ANTIBODY, AND METHODS OF USING SAME

[75] Inventors: Graham P. Allaway, Mohegan Lake; Paul J. Maddon, New York, both of N.Y.

[73] Assignee: Progenics Pharmaceuticals, Inc., Tarrytown, N.Y.

[21] Appl. No.: 21,879

[22] Filed: Feb. 24, 1993

[51] Int. Cl.$^6$ ............... C07K 16/46; C07K 16/10; A61K 39/42

[52] U.S. Cl. .................. 530/387.3; 424/134.1; 424/139.1; 424/148.1; 424/154.1; 424/160.1; 530/387.9; 530/388.35

[58] Field of Search ............... 424/85.8, 86, 89, 424/134.1, 148.1, 154.1, 208.1, 133.1, 139.1, 160.1; 435/5, 70.21, 172.2, 172.3, 69.6, 240.27, 320.1, 252.3; 514/2, 8, 12; 530/350, 380, 387.3, 388.35, 387.9

[56] References Cited

PUBLICATIONS

Fahcy et al., *Clin Exp Immunol.* 88:1–5, 1992.
Sandstrom et al., *Drugs* 34:372–390, 1987.
Allaway et al., *AIDS Res. Hum. Retroviruses* 9(7):581–587, 1993.
Tilley et al., VII Intl. Conference on AIDS, Jun., 1991, Abstract #M.A. 70.
Tilley et al., *6th Collogue Des Cent Gardes,* pp. 211–216, 1991.
Kennedy et al., *AIDS Res. Hum. Retroviruses* 7(12):975–981, 1991.
Capon et al., *Nature* 337:525–531, 9 Feb. 1989.
Traunecker et al., *Nature* 339:68–70, 4 May 1989.
Byrn et al., *Nature* 344:667–670, 12 Apr. 1990.
Ward et al., Nature 352:434–436, 1 Aug. 1991.
Kennedy, M.S., et al., Analysis of Synergism/Antagonism Between HIV–1 Antibody–Positive Human Sera and Soluble CD4 in Blocking HIV–1 Binding and Infectivity, AIDS Research and Human Retroviruses, vol. 7, No. 12, pp. 975–981 (1991). (Exhibit B).
Potts, B.J., et al., Synergistic Inhibition of HIV–1, Keystone Symposia on Molecular and Cellular Biology — Prevention and Treatment of AIDS, printed in Journal of Cellular Biochemistry, Abstract No. Q444, Supplement 16E (1992). (Exhibit C).
McKeating, J.A., et al., Synergistic Interaction Between Ligands Binding to the CD4 Binding Site and V3 Domain Immunodeficiency Virus Type I gpl20, Virology, vol. 191, pp. 732–742 (1992). (Exhibit D).

*Primary Examiner*—Robert D. Budens
*Attorney, Agent, or Firm*—John P. White; Cooper & Dunham LLP

[57] ABSTRACT

The invention is directed to compositions containing CD4-based immunoconjugates and antibodies specific for the envelope glycoprotein of human immunodeficiency virus type 1 (HIV-1). The CD4-based immunoconjugates comprise a portion obtained from CD4 conjugated to a heavy or light chain region obtained from IgG2. The CD4-immunoconjugates can be CD4-IgG2 chimeric heavy chain homodimers whose chains are encoded by the expression vector designated CD4-IgG2-pcDNA1 having ATCC Accession No. 40952, or heterotetramers having chimeric heavy chains encoded by the expression vector designated CD4-IgG2HC-pRcCMV having ATCC Accession No. 75193 and chimeric light chains encoded by the expression vector designated CD4-kLC-pRcCMV having ATCC Accession No. 75194. The compositions of the invention act synergistically to neutralize HIV-1.

6 Claims, 3 Drawing Sheets

SYNERGISTIC COMPOSITION OF CD4-BASED PROTEIN AND ANTI-HIV-1 ANTIBODY, AND METHODS OF USING SAME

BACKGROUND OF THE INVENTION

Throughout this application, various publications are referenced by Arabic numerals. Full citations for these publications may be found at the end of the specification immediately preceding the claims. The disclosure of these publications is hereby incorporated by reference into this application to describe more fully the art to which this invention pertains.

i) Early events in HIV infection HIV-1 is the primary causal agent of Acquired Immunodeficiency Syndrome (AIDS). In infected people, HIV-1 infects primarily helper T lymphocytes, monocytes/macro-phages and dendritic cells--cells that express surface CD4. HIV-1-infected helper T lymphocytes die, and the loss of these CD4+ T lymphocytes is one marker of the progress of HIV-1 infection. The depletion of these cells is probably an important cause of the loss of immune function, resulting in the development of the opportunistic infections and malignancies which typify AIDS. Unlike helper T lymphocytes, other CD4+ cells such as dendritic cells and monocyte/macrophages may become chronically infected by HIV-1. These cells produce virus over a long period of time and appear to be major reservoirs of virus in vivo (1, 2).

The initial phase of the HIV-1 replicative cycle involves the high affinity interaction between the HIV-1 exterior envelope glycoprotein gp120 and the HIV-1 receptor CD4 (Kd approximately $4 \times 10^{-9}$ M) (3). Following the attachment of HIV-1 to cell surface CD4, viral and target cell membranes fuse, resulting in the introduction of the viral capsid into the target cell cytoplasm. The process of fusion has not been fully elucidated. There is evidence that when CD4 binds to gp120, a conformational change occurs in gp120 (4). It is probable, by analogy with other enveloped viruses, that this conformational change results in the exposure of the hydrophobic domain of gp41, which then penetrates the target cell membrane. HIV-1 fusion appears to occur at the cell surface in a pH-independent manner, similar to the fusion of well studied viruses such as Semliki Forest Virus, but unlike the fusion of viruses such as Influenza which are endocytosed and require acidic conditions to trigger fusion (5).

ii) CD4-based therapeutics

A number of therapeutic strategies have been proposed using CD4-based molecules to target HIV-1 or HIV-1-infected cells which express gp120. These strategies are advantageous in that they depend on the interaction between CD4 and gp120. This interaction is essential for virus infection, so CD4-based strategies should be effective against most, if not all, strains of HIV-1. Moreover, it is highly unlikely that escape mutants would develop with mutations in gp120 which eliminate CD4 binding.

In one example of CD4-containing therapies, a soluble version of the entire extracellular segment of CD4 (V1–V4), termed sCD4, has been developed (6). In vitro experiments demonstrate that: 1) sCD4 acts as a "molecular decoy" by binding to HIV-1 gp120 and inhibiting viral attachment to, and subsequent infection of, human cells; 2) sCD4 "strips" the viral envelope glycoprotein gp120 from the viral surface; and 3) sCD4 blocks the intercellular spread of virus from HIV-1-infected cells to uninfected cells by inhibiting virus-mediated cell fusion (7).

In addition to in vitro results, experiments with sCD4 in simian immunodeficiency virus (SIV)-infected rhesus monkeys have been described. These studies demonstrate that administration of sCD4 to SIV-infected rhesus monkeys leads to a diminution of the viral reservoir.

Phase I human clinical trials with sCD4 demonstrate that there is no significant toxicity or immunogenicity associated with the administration of sCD4 at doses as high as 30 mg/day. Preliminary antiviral studies were inconclusive with respect to CD4 cell count and levels of HIV-1 antigen (8, 9).

These in vitro animal and human studies with sCD4 defined some limitations. Specifically, the measured serum half-life of sCD4 is very short (45 minutes in humans following intravenous administration) (8, 9). It is hard to imagine that sCD4 administration alone could eliminate HIV-1 from the body. Rather, sCD4 would be used to delay or prevent the spread of infection and the development of disease. Therefore a therapeutic regimen would involve regular treatment with sCD4. However, the short half-life of sCD4 would make it difficult to maintain sufficient levels in the plasma to give a therapeutic effect. This problem is compounded by the fact that higher levels of sCD4 are required to neutralize clinical isolates of HIV-1as compared to laboratory isolates, although all clinical isolates can be neutralized at some concentration (10). To make a CD4-based molecule with a longer half-life, chimeric CD4-based molecules were made which comprise the gp120- binding region of CD4 and a portion of another protein such as an immunoglobulin molecule. Such molecules also have the advantage of greater avidity for HIV-1 based on the multiple gp120-binding domains which they present, compared to sCD4 having only one gp120-binding domain.

For example, dimeric CD4-human IgG1 heavy chain fusion proteins have been described (11, 12). These molecules include a molecule containing the V1V2 domains of CD4 fused to the hinge, CH2 and CH3 domains of a gammal heavy chain (12). These fusion proteins have been used successfully to block HIV-1 infection in vitro, and in one case to block the infection of Chimpanzees by a laboratory strain of HIV-1 (13). The CD4-immunoglobulin chimeras have a significantly longer half-life in vivo than does sCD4 (11). These fusion proteins retain various effector functions of immunoglobulin molecules, such as Fc receptor binding, cell-mediated transfer via an Fc receptor-dependent mechanism, and complement activation (12). Many of the functions of antibodies are mediated through their interaction with Fc receptors. These receptors are found on a variety of cells including macrophages, other leukocytes, platelets and placental trophoblasts (14). The Fc receptor binds to the Fc portion of immunoglobulins and the complex can trigger a variety of responses depending on cell type. In the case of macrophages, the response can include phagocytosis and antibody-dependant cellular cytotoxicity (ADCC). With placental trophoblasts, IgG1 binding leads to transfer of the antibody to the fetus.

The binding of CD4-IgG1 chimeras to Fc receptors has potential drawbacks. In particular, this binding could concentrate virus on Fc receptor-bearing cells such as macrophages, and placental trophoblasts enhance the HIV-1 infection of these cells. In pregnant women, placental transfer of CD4-IgG1 chimeras, when bound to HIV-1, might lead to increased HIV-1 infection of the fetus.

Therefore, CD4-based proteins with little or no effector functions were developed, based on human IgG2 which exhibits little or no Fc receptor binding. These molecules also have an advantage over IgG1-based molecules, in that human IgG2 antibodies exhibit minimal allotypic variation while human IgG1 antibodies have considerable variation. IgG2-based chimeras might be less immunogenic than IgG1 chimeras.

Specifically, a CD4-gamma2 chimeric heavy chain homodimer which contains the V1V2 domains of CD4 linked to the hinge, CH2, and CH3 domains from a human gamma2 heavy chain was produced. A CD4-IgG2 chimeric heterotetramer was also produced. This heterotetramer is composed of chimeric light and heavy chains which are assembled into a tetramer. The heavy chains consist of a segment containing the V1 and V2 domains of CD4 which is fused to a segment containing the CH1, hinge, CH2 and CH3 domains of a human gamma2 heavy chain. The light chains contain the V1 and V2 domains of CD4 fused to the entire constant domain of human kappa light chains.

These CD4-gamma2 chimeric heavy chain homodimers and CD4-IgG2 chimeric heterotetramers block HIV-1 infection and syncytium formation. They have terminal half-lives of 1 or more days in rabbits and do not interact with high affinity Fc receptors on the human monocyte cell line U937. The CD4-IgG2 chimeric heterotetramers may possess increased serum half-lives in humans and increased avidity for HIV-1 as compared with the heavy chain homodimers.

iii) Neutralizing antibodies to HIV-1

During the course of HIV-1 infection in humans, a humoral immune response develops which includes the presence of antibodies which can neutralize HIV-1 infection (15). Early in infection, antibodies to the third variable loop (V3 loop) of gp120 are often detected. Anti-V3 loop antibodies are usually type-specific and neutralize the initial HIV-1 immunogen strain as well as closely related strains (15). In vivo, it appears that escape mutants with modified V3 loops are constantly being selected which are resistant to anti-V3 loop antibodies directed against previous strains. This may be one reason why the immune response to HIV-1 does not succeed in controlling HIV-1 infections.

Neutralizing antibodies to the V3 loop do not block attachment, but appear to act at the fusion step of viral entry (16). This and other data indicate that the V3 loop may have a direct role in fusion, perhaps by interacting with a cellular molecule other than CD4. Mutations in the V3 loop can block fusion. Some reports have suggested that the V3 loop must be cleaved by a cell surface protease prior to fusion, but this hypothesis remains to be proven.

Later in HIV-1 infection, neutralizing antibodies are often detected which target the CD4-binding domain of gp120 and block attachment. These antibodies can neutralize a range of viral strains, probably because the CD4-binding domain of gp120 is highly conserved (15). However, it is clear that these antibodies do not bind to precisely the same site as does CD4 (17), perhaps because CD4 binds to a narrow canyon in gp120 which is too small for penetration by antibodies. Instead, these antibodies may bind to the lip of the canyon where some variability can be tolerated without preventing CD4 binding (17). Therefore, while these antibodies can neutralize a wider variety of HIV-1 strains than antibodies to the V3 loop, they are not as broadly neutralizing as CD4-based molecules. It is unlikely that HIV-1 mutants could develop which are completely resistant to CD4-based molecules yet remain infectious.

Neutralizing antibodies are also found which are directed to other domains of HIV-1 envelope glycoproteins during the course of HIV-1 infection. Of these, antibodies to gp41 are particularly important. These neutralizing antibodies act at the fusion step rather than at the attachment step, and presumably prevent insertion of the fusogenic domain of gp41 into the target membrane. Moreover, unlike anti-V3 loop antibodies, anti-gp41 antibodies can often neutralize a wide range of viral strains (18). This broad neutralization probably results from the more conservative nature of the fusogenic domain of gp41, similar to the CD4-binding domain of gp120 discussed above.

iv) Synergistic compositions of CD4-based proteins and antibodies to gp120 and gp41 for prevention and treatment of HIV-1 infections Recent studies have demonstrated that neutralizing antibodies to the CD4-binding domain of gp120, in combination with anti-V3 loop antibodies, can act synergistically in blocking HIV-1 infection (19–21). As potential therapeutics, these antibodies have some drawbacks. As discussed above, antibodies to the V3 loop neutralize a limited number of HIV-1 strains. The high variability of the V3 loop means that therapeutic use of antibodies to this loop will lead to the selection of resistant HIV-1 strains with different V3 loop sequences. To a lesser extent, this is also true with antibodies to the CD4-binding domain of gp120. As discussed above, antibodies to the CD4-binding domain of gp120 act by blocking attachment. Antibodies to the V3 loop neutralize infection by blocking fusion.

The subject invention provides a composition comprising (a) a CD4-based protein, and (b) an antibody capable of forming a complex with an epitope present on an HIV-1 envelope glycoprotein and of specifically inhibiting HIV-1-envelope glycoprotein-mediated membrane fusion. The composition of the subject invention is a synergistic composition of a molecule which blocks attachment (CD4-based protein) and a molecule which blocks fusion (antibody capable of forming a complex with an epitope present on an HIV-1 envelope glycoprotein). The composition of the subject invention has numerous clinical uses, as described infra.

SUMMARY OF THE INVENTION

The subject invention provides a composition comprising (a) a carrier, (b) a CD4-based protein, and (c) an antibody which specifically binds to an epitope present on an HIV-1 envelope glycoprotein and required for the fusion of a CD4-containing membrane with a membrane containing the HIV-1 envelope glycoprotein, the ratio of CD4-based proteins to antibodies in the composition being such that the ratio of gp120-binding sites on the CD4-based proteins to epitope-binding sites on the antibodies is between about 0.01 and about 100.

Desirably, the ratio of gp120-binding sites to epitope-binding sites is between about 0.1 and about 10. Thus, the ratio of gp120-binding sites to epitope-binding sites may be between about 1 and about 10. For example, the ratio may be between about 1.5 and about 6.

In one embodiment, the carrier is a pharmaceutically acceptable carrier. For example, the composition may be a liquid and the pharmaceutically acceptable carrier may be an aqueous buffer. Alternatively, the composition may be a solid and the pharmaceutically acceptable carrier may be an excipient.

In one embodiment, the CD4-based protein is sCD4. In another embodiment, the CD4-based protein is a CD4-immunoconjugate.

For example, the CD4-immunoconjugate may be a CD4-gammal chimeric heavy chain homodimer. The CD4-immunoconjugate may also be a heterotetramer comprising two heavy chains and two light chains, both heavy chains being either a) IgG1 heavy chains or b) chimeric CD4-IgG1 heavy chains, and both light chains being a) kappa light chains, b) lambda light chains c) chimeric CD4-kappa light chains, or d) chimeric CD4-lambda light chains, with the proviso that either both heavy chains or both light chains or all four chains are CD4 chimeras. The heterotetramer may be a heterotetramer wherein the chimeric CD4-IgG1 heavy chains are encoded by the expression vector designated CD4-IgG1 HC-pRcCMV (ATCC No. 75192), and the chimeric CD4-kappa light chains are encoded by the expression vector designated CD4-kLC-pRcCMV (ATCC No. 75194).

The CD4-immunoconjugate may be a CD4-gamma2 chimeric heavy chain homodimer. The CD4-gamma2 chimeric heavy chain homodimer may be the CD4-gamma2 chimeric heavy chain homodimer whose chains are encoded by the expression vector designated CD4IgG$_2$-pcDNA1 (ATCC No. 40952).

The CD4-immunoconjugate may also be a heterotetramer comprising two heavy chains and two light chains, both heavy chains being either a) IgG2 heavy chains or b) chimeric CD4-IgG2 heavy chains, and both light chains being a) kappa light chains, b) lambda light chains c) chimeric CD4-kappa light chains, or d) chimeric CD4-lambda light chains, with the proviso that either both heavy chains or both light chains or all four chains are CD4 chimeras. The heterotetramer may be a heterotetramer wherein the chimeric CD4-IgG2 heavy chains are encoded by the expression vector designated CD4-IgG2HC-pRcCMV (ATCC No. 75193), and the chimeric CD4-kappa light chains are encoded by the expression vector designated CD4-kLC-pRcCMV (ATCC No. 75194).

In one embodiment, the antibody is capable of forming a complex with an epitope present on HIV-1 gp120 envelope glycoprotein. For example, the antibody may be capable of forming a complex with an epitope present on the V3 loop of HIV-1 gp120 envelope glycoprotein.

In the preferred embodiment, the antibody is capable of forming a complex with an epitope present on HIV-1 gp41 envelope glycoprotein. For example, the antibody may be capable of forming a complex with an epitope present on HIV-1 gp41 envelope glycoprotein, said epitope comprising the amino acid sequence ELDKWA (SEQ ID NO:1). The antibody may be the monoclonal antibody designated 2F5.

The subject invention also provides a method of treating a subject which comprises administering to the subject an amount of the composition of the subject invention effective to reduce the likelihood of the subject's becoming infected with HIV-1.

The subject may be a newborn infant. The subject may also be a medical practitioner.

The subject invention further provides a pharmaceutical composition comprising an amount of the composition of the subject invention effective to reduce the likelihood of a subject's becoming infected with HIV-1.

The subject invention further provides a method of treating an HIV-infected subject, which comprises administering to the subject an amount of the composition of the subject invention effective to reduce the rate of spread of HIV-1 infection in the subject.

The subject invention further provides a pharmaceutical composition comprising an amount of the composition of the subject invention effective to reduce the rate of spread of HIV-1 infection in an HIV-1-infected subject.

The subject invention further provides a method of decontaminating a fluid containing HIV-1, which comprises contacting the fluid with the composition of the subject invention, under conditions such that the composition of the subject invention forms a complex with the HIV-1 therein, thereby decontaminating the fluid.

Finally, the subject invention provides a method of decontaminating a fluid containing HIV-1, which further comprises contacting the fluid with the composition of the subject invention, under conditions such that the composition of the subject invention forms a complex with the HIV-1 therein, and removing the complex so formed from the fluid, thereby decontaminating the fluid.

BRIEF DESCRIPTION OF THE FIGURES

FIG. 1: Inhibition of HIV-1-envelope induced cell fusion by sCD4 (▲—▲), an antibody to the V3 loop of HIV-1 gp120 (designated 9205) (●—●) and a 1:1 composition (on a mass basis) of the two (♦—♦).

FIG. 2: Median effect plot of data in FIG. 1. The Log (fraction inhibited/fraction uninhibited) is plotted against Log dose for sCD4 alone (▲—▲), the anti-V3 loop antibody 9205 (●—●) and a 1:1 composition (on a mass basis) of the two (♦—♦).

FIG. 3: Combination index plotted against fractional inhibition for the sCD4/9205 synergy analysis. The method of Chou and Talalay (23) was used for the calculations, where a CI of 1 indicates additivity, <1 indicates synergy and >1 indicates antagonism. The more conservative mutually non-exclusive calculation method was used.

DETAILED DESCRIPTION OF THE INVENTION

The plasmids $CD4-IgG_1HC$-pRcCMV, CD4-kLC-pRcCMV, $CD4IgG_2$-pcDNA1 and $CD4-IgG_2HC$-pRcCMV were deposited pursuant to, and in satisfaction of, the requirements of the Budapest Treaty on the International Recognition of the Deposit of Microorganisms for the Purposes of Patent Procedure with the American Type Culture Collection (ATCC), 12301 Parklawn 10 Drive, Rockville, Md. 20852 under ATCC Accession Nos. 75192, 75194, 40952, and 75193, respectively. The plasmids $CD4-IgG_1$ HC-pRcCMV, CD4-kLC-pRcCMV, and $CD4-IgG_2HC$-pRcCMV were deposited with the ATCC on Jan. 30, 1992. The plasmid $CD4IgG_2$-pcDNA1 was deposited with the ATCC on Jan. 31, 1991.

Specifically, the subject invention provides a composition comprising (a) a carrier, (b) a CD4-based protein, and (c) an antibody which specifically binds to an epitope present on an HIV-1 envelope glycoprotein and required for the fusion of a CD4-containing membrane with a membrane containing the HIV-1 envelope glycoprotein, the ratio of CD4-based proteins to antibodies in the composition being such that the ratio of gp120-binding sites on the CD4-based proteins to epitope-binding sites on the antibodies is between about 0.01 and about 100.

As used herein, CD4 means the mature, native, membrane-bound CD4 protein comprising a cytoplasmic domain, a hydrophobic transmembrane domain, and an extracellular domain which binds to HIV-1 gp120 envelope glycoprotein.

As used herein, a CD4-based protein is any protein comprising at least one sequence of amino acid residues corresponding to that portion of CD4 which is required for CD4 to form a complex with the HIV-1 gp120 envelope glycoprotein. If the CD4-based protein is sCD4, then the sequence of amino acid residues corresponding to that portion of CD4 which is required for CD4 to form a complex with the HIV-1 gp120 envelope glycoprotein is the amino acid sequence from +1 to about +106. As used herein, sCD4 means a water soluble, extracellular fragment of human CD4. If the CD4-based protein comprises a portion of a non-CD4 protein, then the sequence of amino acid residues corresponding to that portion of CD4 which is required for CD4 to form a complex with the HIV-1 gp120 envelope glycoprotein is the amino acid sequence from +1 to about +179. Thus, a CD4-based protein is a protein which includes one or more gp120-binding sites.

Examples of CD4-based proteins include, but are in no way limited to, the CD4-based proteins discussed infra.

As used herein, "fusion of a CD4-containing membrane with a membrane containing the HIV-1 envelope glycoprotein" means the hydrophobic joining and integration of the CD4-containing membrane with the membrane containing the HIV-1 envelope glycoprotein, and not the CD4-HIV-1 envelope glycoprotein-mediated binding of the CD4-containing membrane to the membrane containing the HIV-1 envelope glycoprotein, which binding is a prerequisite for the fusion. The membrane containing the HIV-1 envelope glycoprotein may be an HIV-1 viral membrane. The membrane containing the HIV-1 envelope glycoprotein may also be a cellular membrane containing the HIV-1 envelope glycoprotein.

As used herein, the ratio of gp120-binding sites on the CD4-based protein to HIV-1 envelope glycoprotein epitope-binding sites on the antibody means the ratio of the number of moles of gp120-binding sites on the CD4-based protein in the composition to the number of moles of HIV-1 envelope glycoprotein-binding sites on the antibody in the composition. For example, if a composition comprises x moles of a CD4-based protein having one gp120-binding site per molecule, and y moles of an antibody having two HIV-1 envelope glycoprotein epitope-binding sites per antibody, then the ratio of gp120-binding sites on the CD4-based protein to HIV-1 envelope glycoprotein epitope-binding sites on the antibody would be x:2y.

Desirably, the ratio of gp120-binding sites to epitope-binding sites is between about 0.1 and about 10. Thus, the ratio of gp120-binding sites to epitope-binding sites may be between about 1 and about 10. For example, the ratio may be between about 1.5 and about 6.

In one embodiment, the carrier is a pharmaceutically acceptable carrier. For example, the composition may be a liquid and the pharmaceutically acceptable carrier may be an aqueous buffer. Alternatively, the composition may be a solid and the pharmaceutically acceptable carrier may be an excipient.

Pharmaceutically acceptable carriers are well known to those skilled in the art and include, but are not limited to, 0.01–0.1M and preferably 0.05M phosphate buffer or 0.8% saline. Additionally, such pharmaceutically acceptable carriers may be aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's or fixed oils. Intravenous vehicles include fluid and nutrient replenishers, electrolyte replenishers such as those based on Ringer's dextrose, and the like. Preservatives and other additives may also be present, such as, for example, antimicrobials, antioxidants, chelating agents, inert gases and the like.

In one embodiment, the CD4-based protein is sCD4. In another embodiment, the CD4-based protein is a gp120-binding fragment of sCD4.

In another embodiment, the CD4-based protein is a CD4-immunoconjugate. As used herein, a CD4-immunoconjugate is a molecule which comprises the gp120-binding portion of CD4 and an Fc immunoglobulin domain, or biologically active portion thereof.

The CD4-immunoconjugate may be a CD4-gammal chimeric heavy chain homodimer. The CD4-immunoconjugate may also be a heterotetramer comprising two heavy chains and two light chains, both heavy chains being either a) IgG1 heavy chains or b) chimeric CD4-IgG1 heavy chains, and both light chains being a) kappa light chains, b) lambda light chains c) chimeric CD4-kappa light chains, or d) chimeric CD4-lambda light chains, with the proviso that either both heavy chains or both light chains or all four chains are CD4 chimeras. The heterotetramer may be a heterotetramer wherein the chimeric CD4-IgG1 heavy chains are encoded by the expression vector designated CD4-IgG1 HC-pRcCMV (ATCC No. 75192), and the chimeric CD4-kappa light chains are encoded by the expression vector designated CD4-kLC-pRcCMV (ATCC No. 75194).

The CD4-immunoconjugate may be a CD4-gamma2 chimeric heavy chain homodimer. The CD4-gamma2 chimeric heavy chain homodimer may be the CD4-gamma2 chimeric heavy chain homodimer whose chains are encoded by the expression vector designated CD4IgG$_2$-pcDNA1 (ATCC No. 40952).

The CD4-immunoconjugate may also be a heterotetramer comprising two heavy chains and two light chains, both heavy chains being either a) IgG2 heavy chains or b) chimeric CD4-IgG2 heavy chains, and both light chains being a) kappa light chains, b) lambda light chains c) chimeric CD4-kappa light chains, or d) chimeric CD4-lambda light chains, with the proviso that either both heavy chains or both light chains or all four chains are CD4 chimeras. The heterotetramer may be a heterotetramer wherein the chimeric CD4-IgG2 heavy chains are encoded by the expression vector designated CD4-IgG2HC-pRcCMV (ATCC No. 75193), and the chimeric CD4-kappa light chains are encoded by the expression vector designated CD4-kLC-pRcCMV (ATCC No. 75194).

In the preferred embodiment, the CD4-immunoconjugate is either a CD4-gamma2 chimeric heavy chain homodimer or a CD4-IgG2 chimeric heterotetramer.

In one embodiment, the antibody is capable of forming a complex with an epitope present on HIV-1 gp120 envelope glycoprotein. The antibody may be capable of forming a complex with an epitope present on the V3 loop of HIV-1 gp120 envelope glycoprotein.

In the preferred embodiment, the antibody is capable of forming a complex with an epitope present on HIV-1gp41 envelope glycoprotein. The antibody may be capable of forming a complex with an epitope present on HIV-1 gp41 envelope glycoprotein, said epitope comprising the amino acid sequence ELDKWA (SEQ ID NO:2). The antibody may be the monoclonal antibody designated 2F5.

The subject invention also provides a method of treating a subject which comprises administering to the subject an amount of the composition of the subject invention effective to reduce the likelihood of the subject's becoming infected with HIV-1.

As used herein, reducing the likelihood of the subject's becoming infected with HIV-1 means reducing the likelihood of the subject's becoming infected with HIV-1 by at least two-fold. For example, if a subject has a 1% chance of becoming infected with HIV-1, a two-fold reduction in the likelihood of the subject's becoming infected with HIV-1 would result in the subject's having a 0.5% chance of becoming infected with HIV-1. In a preferred embodiment of this invention, reducing the likelihood of the subject's becoming infected with HIV-1 means reducing the likelihood of the subject's becoming infected with HIV-1 by at least ten-fold.

The subject may be a human. The subject may also be an individual recently exposed to HIV-1.

In one embodiment, the subject is a newborn infant. The newborn infant may be a newborn infant born to an HIV-1-infected mother.

In another embodiment, the subject is a medical practitioner. The medical practitioner may be a medical practitioner exposed to an HIV-1-containing bodily fluid. As used herein, the term "medical practitioner" includes, but is in no way limited to, doctors, dentists, surgeons, nurses, medical laboratory assistants, and students in health care programs.

As used herein, "the subject's becoming infected with HIV-1" means the invasion of the subject's own cells by HIV-1.

As used herein, administering may be effected or performed using any of the various methods known to those skilled in the art. The administering may comprise administering intravenously. The administering may also comprise administering intramuscularly. The administering may further comprise administering subcutaneously.

The amount of the composition of the subject invention effective to reduce the likelihood of the subject's becoming infected with HIV-1 may be readily determined using methods well known to those skilled in the art. In the preferred embodiment, the amount is between about 0.1 mg/kg and 10mg/kg of body weight.

The subject invention further provides a pharmaceutical composition comprising an amount of the composition of the subject invention effective to reduce the likelihood of the subject's becoming infected with HIV-1.

The subject invention further provides a method of treating an HIV-infected subject, which comprises administering to the subject an amount of the composition of the subject invention effective to reduce the rate of spread of HIV-1 infection in the subject.

The subject may be a human. As used herein, an "HIV-infected subject" means an individual having at least one of his own cells invaded by HIV-1.

As used herein, reducing the rate of spread of HIV-1 infection in the subject means reducing the rate of spread by at least two-fold. For example, if the rate of spread of HIV-1 infection were x cells invaded by HIV-1per given unit of time, a two-fold reduction in the rate of spread of HIV-1 infection would result in ½x cells invaded by HIV-1 per given unit of time. In a preferred embodiment of this invention, reducing the rate of spread of HIV-1 infection in the subject means reducing the rate of spread by at least ten-fold.

The amount of the composition of the subject invention effective to reduce the rate of spread of HIV-1 infection in the subject may be readily determined using methods well known to those skilled in the art. In the preferred embodiment, the amount is between about 0.1 mg/kg and 10mg/kg of body weight.

The subject invention further provides a pharmaceutical composition comprising an amount of the composition of the subject invention effective to reduce the rate of spread of HIV-1 infection in an HIV-1-infected subject.

The subject invention further provides a method of decontaminating a fluid containing HIV-1, which comprises contacting the fluid with the composition of the subject invention, under conditions such that the composition of the subject invention forms a complex with the HIV-1 therein, thereby decontaminating the fluid.

As used herein, "decontaminating a fluid containing HIV-1" means either (a) rendering the HIV-1 in the fluid unable to invade cells, (b) removing the HIV-1 from the fluid, or (c) a combination of (a) and (b).

As used herein, the term "fluid" includes, but is not limited to, a bodily fluid. A bodily fluid is any fluid which is present in the human body and is capable of containing infectious HIV in an HIV-infected patient. Bodily fluids include, but are not limited to, blood or derivatives thereof, saliva, cerebrospinal fluid, tears, vaginal secretions, urine, alveolar fluid, synovial fluid, pleural fluid and bone marrow. The fluid may be a fluid which is to be administered to a subject.

Conditions under which the composition of the subject invention would form a complex with HIV-1 are well known to those skilled in the art.

Finally, the subject invention provides a method of decontaminating a fluid containing HIV-1, which further comprises contacting the fluid with the composition of the subject invention, under conditions such that the composition of the subject invention forms a complex with the HIV-1 therein, and removing the complex so formed from the fluid, thereby decontaminating the fluid.

Removing the complex formed between the composition of the subject invention and the HIV-1 from the fluid may be accomplished according to methods well known to those skilled in the art. By way of example, the complex may be removed by contacting the fluid containing the complex with an immobilized antibody specific for the complex, thereby removing the complex from the fluid. An antibody specific for the complex may be obtained according to methods well known to those skilled in the art. Furthermore, methods of immobilizing antibodies are well known to those skilled in the art.

This invention will be better understood by reference to the Experimental Details which follow, but those skilled in the art will readily appreciate that the specific experiments detailed are only illustrative of the invention as described more fully in the claims which follow thereafter.

EXPERIMENTAL DETAILS

A. Materials and Methods i) Reagents a) General sCD4, CD4-gamma1 chimeric heavy chain homodimers, CD4-gamma2 chimeric heavy chain homodimers and CD4-IgG2 chimeric heterotetramers were obtained from Progenics Pharmaceuticals, Inc. (Tarrytown, N.Y.). Mouse antibody [9205] to the V3 loop of gp120, derived from the HIV-$1_{HTLVIIIB}$ isolate (24), was obtained from DuPont NEN Research Products (Wilmington, Del.). Human antibody 2F5 to a conserved epitope of HIV-1 gp41 (18) was obtained from Viral Testing Systems Corporation (Houston, Tex.) and from Waldheim Pharmazeutika (Vienna, Austria).

b) sCD4

Soluble CD4 (a genetically-engineered, water-soluble extracellular fragment of human CD4) is disclosed, for example, in Patent Cooperation Treaty International Publication No. WO 88/01304. Soluble CD4 is also commercially available.

Soluble CD4, also designated sCD4, may be produced by truncating pT4B (ATCC No. 68389) after the V4J4 domain.

Such DNA fragments terminate before the transmembrane segment, which begins at approximately nucleotide position 1264.

Purification and characterization of soluble CD4 fragments is greatly enhanced by constructing a cell line (preferably mammalian) which overexpresses the secreted protein fragment. Strategies which allow the overexpression of proteins may be employed in bacteria, yeast, insect and mammalian systems. Inducible expression systems may also be employed in bacteria and yeast to overproduce proteins which may be toxic if constitutively expressed. Overexpression of soluble CD4 fragments may be accomplished by amplifying a soluble CD4 expression vector, resulting in constitutive overexpression. The amplification of dihydrofolate reductase (dhfr) genes by growth in progressively increased concentrations of the drug methotrexate, an antagonist of dhfr, is widely employed. Since the amplified unit is not limited to dhfr coding sequences, this approach results in the coamplification of sequences adjacent to them. Therefore, dhfr may be used as a selectable marker and as a means of coamplifying newly introduced sequences. This strategy may be successfully employed to increase the expression of several different genes cotransformed with dhfr plasmids.

Using recombinant DNA technology, a vector expressing a secreted, soluble, extracellular fragment of CD4 encoded by the human cDNA clone pT4B may be generated. Base pairs 1-1252 of pT4B encode the leader peptide of CD4 needed for the synthesis of secreted protein, as well as the extracellular portion of CD4 encompassing the four VJ-like domains (V1J1-V4J4), but not the transmembrane and cytoplasmic regions which anchor the protein in the membrane. This vector contains sequences encoding the extracellular portion of the CD4 protein which contains the HIV binding domain. These sequences are placed downstream from the SV40 early region promoter. In addition, a TAA termination codon followed by the polyadenylation region of the bovine growth hormone gene is placed downstream from the truncated CD4 cDNA to provide the signals necessary for the termination of protein synthesis, transcription termination, and polyadenylation of the RNA transcript. The resulting soluble CD4 minigene is then ligated to the mouse dihydrofolate reductase (dhfr) gene to generate a plasmid capable of being amplified after introduction into dhfr-deficient (dhfr-) Chinese hamster ovary (CHO) cells.

For example, the 1.8 kb EcoRI-BamHI fragment of pT4B, which contains the entire CD4 coding sequence, is inserted between the StuI and BclI sites of the mammalian expression vector DSP modified to contain the SV-40 early promoter and the bovine growth hormone polyadenylation sequence. Through the use of synthetic linkers, the HaeII (bp 124)-HpaII (bp 1252) fragment of pT4B is inserted between the KpnI and XbaI sites of the plasmid pUC18. A soluble CD4 expression vector is created by ligating:

1. a 0.95 kb BglII-SacI fragment of modified DSP which contains the 1.8 kb EcoRI-BamHI fragment of pT4B (this segment contains the SV40 early promoter, the CD4 leader sequence, and the amino terminal portion of the extracellular CD4 sequence);
2. the 0.66 kb SacI-XbaI fragment of the pUC18 plasmid containing the HaeII-HpaII fragment of pT4B (this segment contains the carboxy terminal portion of the extracellular CD4 sequence followed by a TAA termination codon inserted after valine 371); and
3. the 2.48 kb BglII-XbaI fragment of modified DSP which contains the bovine growth hormone polyadenylation sequence.

Finally, the 2.2 kb BglII-BamHI fragment from another modified DSP containing a mouse dhfr expression cassette (β-globin promoter-mouse dhfr coding region-SV40 polyadenylation region) flanked by BglII and BamHI sites, is inserted into the BamHI site of a plasmid to create a soluble CD4 expression plasmid.

DXB-11, a clone of Chinese hamster ovary cells deficient in dhfr, is transfected with the soluble CD4 expression plasmid. The DXB-11 transformants are then grown in F12 medium, without hypoxanthine or thymidine, containing 10% dialyzed fetal bovine serum. Clones are selected and subjected to stepwise increasing concentrations of methotrexate (mtx), an antagonist of dhfr, to select for stable transformants which have amplified the newly introduced dhfr gene and adjacent soluble CD4 sequences.

Purification of the sCD4 protein was performed using ion exchange chromatography. Ion exchange chromatography is well known to those skilled in the art.

c) CD4-IqG1 Chimeras

Co-expression of CD4-IqG1HC-pRcCMV and CD4-kLC-pRcCMV in mammalian cells to produce CD4-IaG1 chimeric heterotetramer Stable expression Dhfr- Chinese hamster ovary cells (CHO) are transfected with 20 micrograms of CsCl purified DNA in a ratio of 1000:1000:1 CD4-IgG1 HC-pRcCMV:CD4-kLC-pRcCMV:p410 (p410 is an expression plasmid containing the dhfr gene), although other ratios may also be used. At approximately 3–5 days post-transfection, cells are placed in selective medium (nucleoside-free alpha MEM containing 5% dialyzed fetal calf serum). At approximately 10–15 days post-selection, individual cell clones are picked. The clones are then analyzed for stable expression of CD4-IgG1 chimeric heterotetramers by several screening techniques, such as ELISA and precipitation with Protein A-sepharose beads followed by SDS-PAGE under reducing or non-reducing conditions. Clones expressing the highest levels are subjected to successive rounds of amplification of the newly introduced DNA sequences in increasing concentrations of methotrexate. Stable CHO cell lines are thus generated which secrete high levels of CD4-IgG1 chimeric heterotetramer.

Purification of CD4-IgG1 chimeric heterotetramers from CHO conditioned media

CD4-IgG1 chimeric heterotetramers are purified using Protein A-Sepharose column chromatography. CHO cells secreting CD4-IgG1 chimeric heterotetramers are grown to high density in roller bottles in medium containing alpha MEM with 5% IgG-free fetal calf serum. Conditioned media is collected, clarified by centrifugation, and diluted 1:1 with PBS either with or without detergent (i.e. Tween) in this and subsequent buffers. The diluted media is then applied to a 5 ml column of Protein A-Sepharose fast flow previously equilibrated with PBS, at a flow rate of 60 ml/hour. After extensive washing, the bound material is eluted with 100 mM glycine/HCl, pH 3.5, directly into an aliquot of 1M Tris.HCl pH 8.0 to immediately neutralize the eluted fractions. Fractions are then analyzed by SDS-PAGE under reducing and non-reducing conditions followed by silver staining and pooled.

The pooled fractions were then applied to a 10 ml column of S-sepharose fast flow previously equilibrated with 50 mM BES pH 7.0 at a flow rate of 120 ml/hr. After application of the sample, a step elution gradient (consisting of the following 4 steps: 5 column volumes of 50 mM BES pH 7.0, 4 column volumes of 50 mM BES pH 7.0, 100 mM NaCl, 6 column volumes of 50 mM BES pH 7.0 225 mM NaCl, followed by 8 column volumes of 50 mM BES pH 7.0, 500 mM NaCl) was employed for specific elution of the CD4-IgG1 chimeric heterotetramer. The CD4-IgG1 chimeric heterotetramer was eluted from the column in 50 mM BES pH 7.0, 500 mM NaCl. The peak fractions were then pooled and concentrated to yield a final protein concentration of at least 1 mg/ml.

d) CD4-IqG2 Chimeras

Stable expression

Dhfr- Chinese hamster ovary cells (CHO) were transfected with 20 micrograms of CsCl-purified DNA in a 1000:1 molar ratio of CD4IgG2-pcDNA1:p410 (p410 is an expression plasmid containing the dhfr gene), although other ratios may also be used. Approximately 3–5 days post-transfection, cells were placed in selective medium (nucleoside-free alpha MEM containing 5% dialyzed fetal calf serum). Approximately 10–15 days post-selection, individual cell clones were picked and analyzed for stable expression of CD4-gamma2 chimeric heavy chain homodimer by several screening techniques, such as ELISA and precipitation with Protein A-sepharose beads followed by SDS-PAGE under reducing and non-reducing conditions. Clones expressing the highest levels were subjected to successive rounds of amplification of the newly introduced DNA sequences in increasing concentrations of methotrexate. Stable CHO cell lines were thus generated which secrete between 10–100 micrograms/milliliter of CD4-gamma2 chimeric heavy chain homodimer.

Purification of CD4-gamma2 chimeric heavy chain homodimer from CHO conditioned media CD4-gamma2 chimeric heavy chain homodimer was purified by column chromatography. CHO cells secreting CD4-gamma2 chimeric heavy chain homodimer were grown to high density in roller bottles in medium containing alpha MEM with 5% IgG-free fetal calf serum. Conditioned media was collected, clarified by centrifugation, and diluted 1:1 with PBS either with or without detergent (i.e. Tween) in this and subsequent buffers. The diluted media was then applied to a 5 ml column of Protein A-Sepharose fast flow previously equilibrated with PBS, at a flow rate of 60 ml/hour. After extensive washing, the specifically bound material was eluted with 100 mM glycine/HCl, pH 3.5, directly into an aliquot of 1M Tris.HCl pH 8.0 to immediately neutralize the eluted fractions. The fractions were then analyzed by SDS-PAGE under reducing and non-reducing conditions followed by silver staining and pooled.

The pooled fractions were then applied to a 10 ml column of S-sepharose fast flow previously equilibrated with 50 mM BES pH 7.0 at a flow rate of 120 ml/hr. After application of the sample, a step elution gradient (consisting of the following 4 steps: 5 column volumes of 50 mM BES pH 7.0, 4 column volumes of 50 mM BES pH 7.0, 100 mM NaCl, 6 column volumes of 50 mM BES pH 7.0 225 mM NaCl, followed by 8 column volumes of 50 mM BES pH 7.0, 500 mM NaCl ) was employed for specific elution of the CD4-gamma2 chimeric heavy chain homodimer. The CD4-gamma2 chimeric heavy chain homodimer was eluted from the column in 50 mM BES pH 7.0, 500 mM NaCl. The peak fractions were then pooled and concentrated to yield a final protein concentration of at least 1 mg/ml. The pooled and concentrated fractions were then applied to a 120 ml column of Sephacryl S-300HR previously equilibrated with PBS, at a flow rate of 8 ml/hr. The CD4-gamma2 chimeric heavy chain homodimer fraction was specifically eluted in PBS, and concentrated to at least 1 mg/ml.

Co-expression of CD4-IgG2HC-pRcCMV and CD4-kLC-pRcCMV in mammalian cells to produce CD4-IgG2 chimeric heterotetramer Stable expression Dhfr- Chinese hamster ovary cells (CHO) are transfected with 20 micrograms of CsCl-purified DNA in a ratio of 1000:1000:1 CD4-IgG2HC-pRcCMV:CD4-kLC-pRcCMV:p410 (p410 is an expression plasmid containing the dhfr gene), although other ratios may also be used. At approximately 3–5 days post-transfection, cells are placed in selective medium (nucleoside-free alpha MEM containing 5% dialyzed fetal calf serum). At approximately 10–15 days post-selection, individual cell clones are picked. The clones are then analyzed for stable expression of CD4-IgG2 chimeric heterotetramers by several screening techniques, such as ELISA and precipitation with Protein A-sepharose beads followed by SDS-PAGE under reducing or non-reducing conditions. Clones expressing the highest levels are subjected to successive rounds of amplification of the newly introduced DNA sequences in increasing concentrations of methotrexate. Stable CHO cell lines are thus generated which secrete high levels of CD4-IgG2 chimeric heterotetramer.

Purification of CD4-IgG2 chimeric heterotetramers from CHO conditioned media

CD4-IgG2 chimeric heterotetramers are purified using Protein A-Sepharose column chromatography. CHO cells secreting CD4-IgG2 chimeric heterotetramers are grown to high density in roller bottles in medium containing alpha MEM with 5% IgG-free fetal calf serum. Conditioned media is collected, clarified by centrifugation, and diluted 1:1 with PBS either with or without detergent (i.e. Tween) in this and subsequent buffers. The diluted media is then applied to a 5 ml column of Protein A-Sepharose fast flow previously equilibrated with PBS, at a flow rate of 60 ml/hour. After extensive washing, the bound material is eluted with 100 mM glycine/HCl, pH 3.5, directly into an aliquot of 1M Tris.HCl pH 8.0 to immediately neutralize the eluted fractions. Fractions are then analyzed by SDS-PAGE under reducing and non-reducing conditions followed by silver staining and pooled.

e) Production of monoclonal anti-gp120 and anti-gp41 antibodies

The anti-gp120 and anti-gp41 monoclonal antibodies used in the subject invention are commercially available. The 9205 monoclonal antibody is available from E. I. du Pont de Nemours & Co., Wilmington, Del., Cat. No. NEA-9205. The 2F5 monoclonal antibody is available from the Institute of Applied Microbiology, Vienna, Austria, Cat. No. IAM41–2F5. It is also possible for one skilled in the art to make human, murine, or humanized murine anti-gp120 or anti-gp41 antibodies by a variety of techniques.

For example it is possible to make human monoclonal anti-gp41 antibodies as described infra. Briefly, peripheral blood mononuclear cells (PBMCs) are isolated from the blood of HIV-1-infected individuals who exhibit anti-gp41 antibodies in their serum. Epstein-Barr Virus (EBV, obtained, for example, from B95-8 cell supernatants) is added to the PBMC preparation which is then plated out in 96-well tissue culture plates at limiting dilution. Colonies of EBV-immortalized B lymphocytes grow out and those colonies producing anti-gp41 antibodies are identified by methods well known to those skilled in the art. For example, the media from these cells is used to immunoprecipitate gp41 from metabolically radio-labelled cells expressing gp120

/gp41. Also, colonies producing anti-gp41 antibodies may be identified by western blotting. Colonies producing monoclonal antibodies specific for the gp41 sequence ELDKWA (SEQ ID NO:1) may be identified by an assay such as the enzyme-linked immunosorbent assay. Briefly, the ELDKWA (SEQ ID NO:1) peptide is synthesized by methods well known to those skilled in the art, or obtained commercially. The ELDKWA (SEQ ID NO:1) peptide is used to coat the wells of a plastic 96 well microtiter plate, and the wells are incubated with dilutions of culture media from individual B lymphocyte colonies. Antibodies which bind to the peptide are identified using, for example, horseradish peroxidase-linked rabbit anti-human immunoglobulin antibodies, followed by peroxidase substrate.

Colonies making the antibodies of interest are expanded and fused with a suitable partner cell line, for example, a mouse/human heteromyeloma. Hybrids are selected by culture in selective medium in the presence of feeder cells, and stable antibody-secreting hybrids are cloned and expanded.

ii) Testing for synergistic blocking of HIV-1 envelope-induced cell fusion by compositions of CD4-based proteins and antibodies to HIV-1 gp120 and gp41

To test the compositions of molecules, a reproducible assay of HIV-1 envelope-mediated membrane fusion was used. Cells expressing the HIV-1 envelope fuse with human cells expressing CD4 to make multinucleated syncytia. The fusion process is initiated by the attachment of HIV-1 gp120 to CD4, followed by HIV-1 envelope-mediated membrane fusion (22). These processes of attachment and fusion are also the initial steps of HIV-1 infection of cells. Syncytium formation is a good model for studying HIV-1 attachment and fusion. Furthermore, anti-viral molecules which block these events also block syncytium formation. HIV-1 envelope-mediated cell fusion is also important, in its own right, as a probable cause of cell death in vivo and as a mechanism for the transmission of HIV-1 from infected to uninfected cells.

In this assay, Chinese Hamster Ovary cells which stably express HIV-1$_{HTLVIIIB}$ gp120 (160G7 cells) are plated out in 96-well tissue culture plates, at a concentration of $2 \times 10^4$ cells per well. In this assay, other cells expressing an HIV-1 envelope glycoprotein may be used instead of 160G7 cells. Such cells expressing an HIV-1 envelope glycoprotein are widely available to those skilled in the art (e.g., NIH AIDS Research and Reference Reagent Program, Catalog No. 1247). Serial dilutions of the CD4-based proteins, antibodies, or a composition of the two are prepared in medium and added to the cells. 5–8 replicate wells are done for each dilution. Two hours later, $2 \times 10^4$ human CD4+ T cells (C8166) are added to each well containing treated 160G7 cells. In this assay, other human CD4+ T cells may be used instead of C8166 cells. Human CD4+ T cells are widely available to those skilled in the art (e.g., NIH AIDS Research and Reference Reagent Program, Catalog No. 404). The plate is returned to 37° C. for 48 hours before counting the syncytia.

Syncytia between the 160G7 cells and C8166 appear as large spherical structures which are easily distinguished from unfused cells using light microscopy at 200x. Two fields of syncytia are counted per well. For a given treatment, the mean number of syncytia per field is calculated and converted into the number of syncytia per well. The degree of inhibition (fraction affected) is calculated in the following manner: the mean number of syncytia per well for a given treatment is subtracted from the control (mean number of syncytia per well in the wells treated with medium alone) and this figure is divided by the control.

Figure 2:
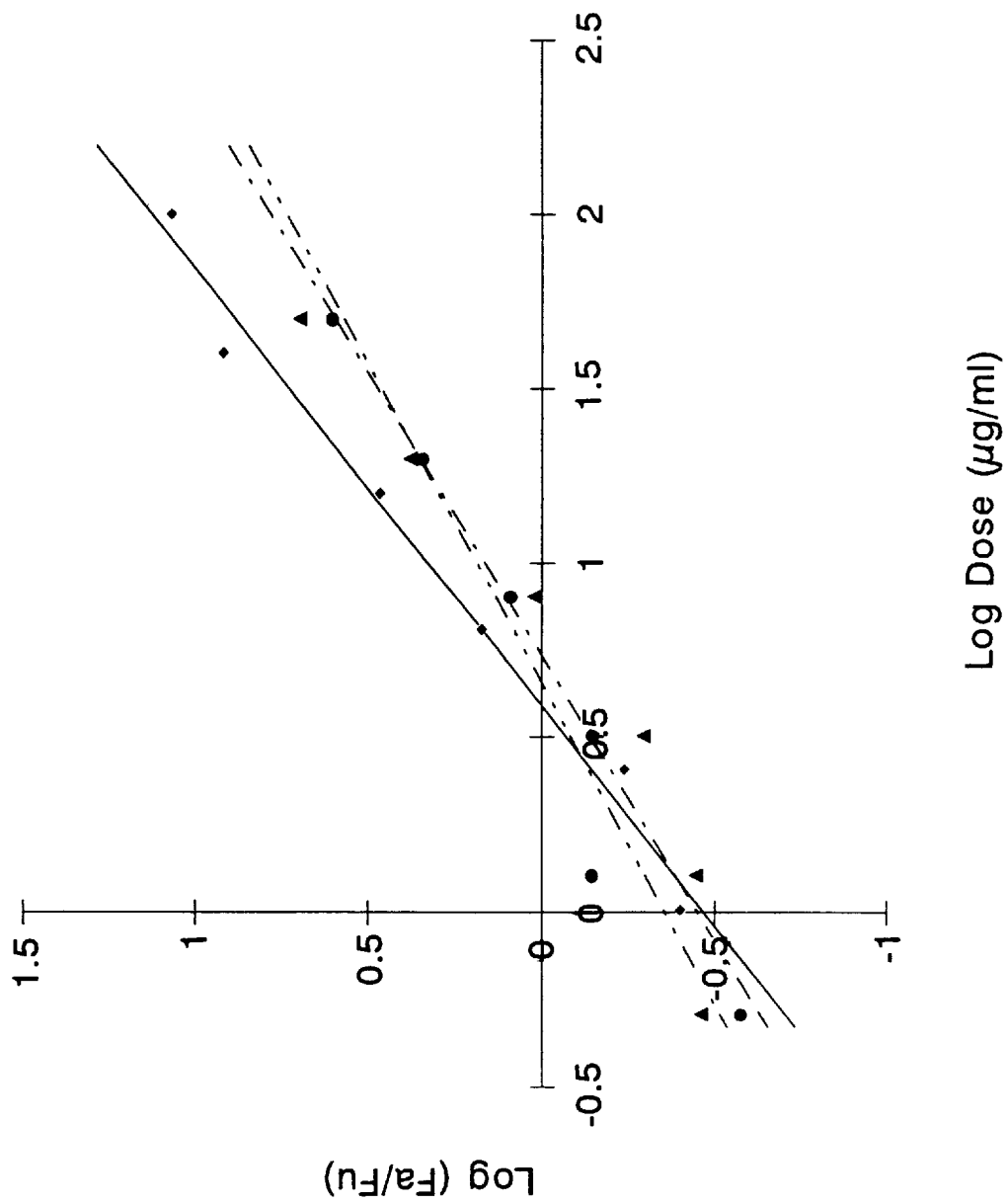
Figure 3:
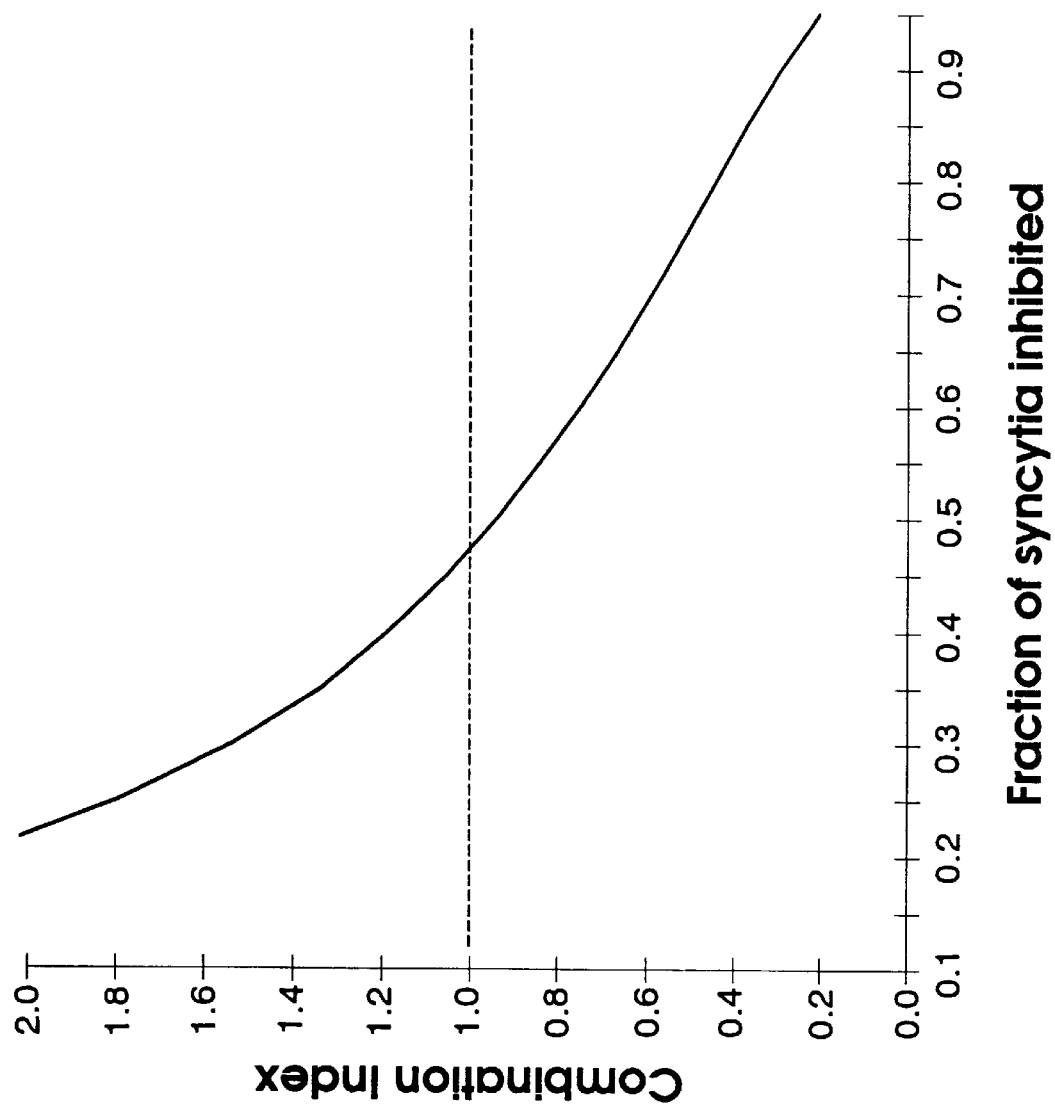

To determine the relationship between the two drugs, the Median Effect method of Chou and Talalay is employed as described in section (iii) below.

iii) Calculation of the relationship between agents: synergy, additivity or antagonism The Combination Index method of Chou and Talalay (23) was used to calculate the degree of synergy, additivity or antagonism between the various agents. The data obtained using the assays above permits calculation of the inhibitory ability of CD4-based molecules and antibodies to gp120 and gp41 both alone and in combination. The dose of CD4-based molecule or antibody is plotted against fractional inhibition as shown in FIG. 1. These data are then transformed using a multiple drug effect analysis based on the median effect principle described by Chou and Talalay (23). This involves a log-log dose response plot (the median effect plot), as shown in FIG. 2, from which the slopes and intercepts are used for computer-assisted calculation of combination indices (CI) at different degrees of inhibition (FIG. 3).

For each molecule, $D_1$, $D_2$, or the combination $D_{1,2}$, the slope (m), median effect dose ($D_m$) and linear correlation coefficient (r) are determined from the median effect plot (23). Next, the dose of each molecule or the combination required to give x fractional inhibition, $(D_x)_1$, $(D_x)_2$, and $(D_x)_{1,2}$, is calculated using the equation:

$$D_x = D_m[x/(1-x)]^{1/m}$$

Next, the contribution of $D_1$ and $D_2$ in the composition $(D_x)_{1,2}$ is calculated from the known dose ratio of the molecules. Finally, the combination index (CI) values are calculated using the equation:

$$CI = \frac{(D)_1}{(D_x)_1} + \frac{(D)_2}{(D_x)_2} + \frac{(D)_1(D)_2}{(D_x)_1(D_x)_2}$$

In these analyses, the mutually non-exclusive calculation method was used (23). This method is most appropriate if the molecules have different target sites, which is probably correct in the case of CD4-based molecules and antibodies to the V3 loop of gp120 or to gp41. Mutually non-exclusive calculations are more conservative and give lower estimates of synergy than mutually exclusive calculations. A CI value of greater than 1 indicates antagonism. A CI value of 1 indicates an additive effect, and a CI value of less than 1 indicates synergy. In general, CI values are most important at the higher levels of inhibition since these correspond to the concentrations of drugs which would be significant in vivo. In the case of the syncytium inhibition assay, 2 or 3 replicates of each experiment were done. These replicates were combined for purposes of analysis.

B. Results and Discussion

Several CD4-based molecules were tested including sCD4, CD4-gamma1 chimeric heavy chain homodimers, CD4-gamma2 chimeric heavy chain homodimers and CD4-IgG2 chimeric heterotetramers. They were tested alone or in combination with antibodies to gp120 or gp41. The antibodies included a mouse antibody [9205] to the V3 loop of gp120 from the HIV-1$_{HTLVIIIB}$ isolate, and a human antibody [2F5] to a conserved epitope of HIV-1 gp41. Table 1 shows the amino-acid sequence specificity of these antibodies.

TABLE 1

Target epitopes of antibodies to gp120 and gp41

| Antibody | Species and Ig subclass | Target Domain on HIV-1 |
|---|---|---|
| 9205 | Mouse IgG1 | gp120 (V3 loop) |
| 2F5 | Human IgG3 | gp41 |

| | Target Epitope | |
|---|---|---|
| Antibody | residue number | amino acid sequence |
| 9205 | 308–322 | RIQRGPGRAFVTIGK (SEQ ID NO: 2) |
| 2F5 | 662–667 | ELDKWA (SEQ ID NO: 2) |

Examples of the analyses are illustrated in FIGS. 1–3. FIG. 1 shows the inhibition of HIV-1 envelope-induced cell fusion by different concentrations of sCD4, anti-V3 loop antibody 9205 and a 1:1 composition thereof (based on mass, equivalent to a 1:3 molar ratio of 9205:sCD4). It is clear that the composition is more effective in blocking than either agent alone. In FIG. 2, this data is transformed to a plot of Log Fa/Fu versus Log dose, where Fa is the fraction affected (fractional inhibition) and Fu is the fraction unaffected (1-fraction affected). The curve for the composition is not parallel with the curves for the individual molecules, supporting the idea that molecules are mutually non-exclusive in their effects (23). FIG. 3 shows CI plotted against fractional inhibition, and demonstrates synergy (CI less than 1) at the higher levels of inhibition.

The same method was used to analyze inhibition of HIV-1 envelope-mediated cell fusion by a number of compositions of CD4-based molecules and antibodies to gp120 and gp41. The results are shown in Table 2.

TABLE 2

Inhibition of HIV-1 envelope-mediated cell fusion by compositions of CD4-based molecules and antibodies to gp41 or the V3 loop of gp120

| | Antibody | IC50 ug/ml | CD4-based molecule | IC50 ug/ml | Molar ratio (Ab/CD4) |
|---|---|---|---|---|---|
| | Anti-V3 loop antibody: | | | | |
| 1. | 9205 | 4.5 | sCD4 | 5.4 | 1:3 |
| 2. | 9205 | 6.6 | gamma1 | 2.8 | 1:1.5 |
| 3. | 9205 | 3.2 | gamma2 | 3.0 | 1:1.5 |
| 4. | 9205 | 3.3 | gamma2 | 2.0 | 1:6 |
| | Anti-gp41 antibody: | | | | |
| 5. | 2F5 | 85.9 | sCD4 | 5.7 | 1:3 |
| 6. | 2F5 | 27.3 | gamma2 | 1.6 | 1:1.5 |

| | Number of Replicates | CI at 75% inhibition | CI at 90% inhibition | CI at 95% inhibition |
|---|---|---|---|---|
| 1. | 3 | 0.52 | 0.30 | 0.21 |
| 2. | 2 | 0.86 | 0.69 | 0.59 |
| 3. | 2 | 0.71 | 0.70 | 0.71 |
| 4. | 2 | 0.74 | 0.59 | 0.52 |
| 5. | 3 | 0.66 | 0.65 | 0.65 |
| 6. | 3 | 0.70 | 0.41 | 0.29 |

Key:
gamma1 = CD4-gamma1 chimeric heavy chain homodimer
gamma2 = CD4-gamma2 chimeric heavy chain homodimer In all cases, an r value greater than 0.9 was obtained for the log/log plots, indicating a good fit between log dose and log Fa/Fu (23). The molar ratio of the molecules in each composition is indicated. In all cases the more conservative mutually non-exclusive calculation method was used. It can be seen from Table 2 that all compositions of molecules tested have combination indices below 1, and therefore are synergistic at higher levels of inhibition (75% inhibition or above), which are most relevant as described supra. For example, the composition of CD4-gamma2 chimeric heavy chain homodimer and monoclonal anti-gp41 antibody is synergistic, with CI values as low as 0.29. This indicates that the amount of the composition required to block HIV-1 envelope-mediated cell fusion is smaller than would be expected based on the blocking abilities of either molecule used alone.

The most useful compositions comprise molecules which can neutralize a wide variety of HIV-1 isolates. The CD4-based molecules fulfill this criterion. Neutralization by antibodies to the V3 loop of gp120 is often limited to a number of closely related isolates, and where this is the case, these antibodies alone would be less useful for blocking HIV-1 infection. In contrast, the anti-gp41 antibody (e.g., 2F5) neutralizes a wider range of isolates (18). Therefore, compositions of CD4-based proteins and antibodies to gp41 may be the most advantageous for clinical use in connection with the prophylaxis and treatment of HIV-1 infection.

When using compositions of molecules in vivo, such as in the case of post-exposure prophylaxis, it is advantageous to use CD4-based molecules with half-lives of one day or more, such as the CD4-gamma2 chimeric heavy chain homodimer or the CD4-IgG2 chimeric heterotetramer. These molecules have advantages over their IgG1 counterparts, particularly in their lack of Fc-mediated function as described supra. In clinical situations, therefore, compositions of the CD4-gamma2 chimeric heavy chain homodimer or CD4-IgG2 chimeric heterotetramer, and broadly neutralizing antibodies such as anti-gp41 antibodies, are particularly advantageous.

C. Examples of clinical uses of the compositions of the subject invention

Example 1
Occupational Exposure to HIV-1

Health care workers exposed to HIV-1-contaminated blood or other bodily fluids can become infected with the virus. Common routes of exposure include, but are in no way limited to, the following: penetration of the skin by an uncapped syringe needle coated with HIV-1-containing bodily fluids ("needle-stick-injury"); cuts caused by scalpels or other instruments during surgery on HIV-1-infected individuals; and splashes of blood or other bodily fluids in the eyes or on cracked skin.

To reduce the risk of HIV-1 transmission in the health care setting, the composition of the subject invention would be administered to a health care worker who was exposed to HIV-1-contaminated fluids, by routes such as those listed above. The composition may be administered by, inter alia, intravenous bolus, continual IV infusion, intramuscular injection, subcutaneous injection or directly to the wound or exposed skin. A combination of these routes may be used. Depending on the route of administration and the nature of the treatment, the composition of the subject invention might be given continuously or intermittently. The treatment may be most effective if the composition were administered as soon after the exposure as possible, for example within one or two hours after exposure.

Example 2
Mother To Infant Transmission Of HIV-1

Newborns of HIV-1-infected mothers often become infected with HIV-1. In many cases, infection occurs around the time of birth, due to the exposure of the baby to HIV-1-contaminated blood and other bodily fluids from the mother.

To reduce the risk of HIV-1 transmission in this setting, the composition of the subject invention would be administered to the mother prior to delivery, or to the baby after delivery, or to both. The possible routes of administration include those listed in Example 1, supra. The purpose of treating the mother would be to reduce the infectivity of the maternal blood or other bodily fluids prior to delivery. As an example, the treatment may comprise delivering to the mother a series of intravenous bolus injections of the composition starting several hours or more before birth. Subsequently, the newborn would be treated with the composition in order to reduce the infectivity of any virus which had entered its body around the time of birth. For example, within one or two hours after birth, the newborn may be treated with a continuous IV infusion of the composition for several days.

References

1. Macatonia, R. L. et al. (1990) Immunology 71, 38–45.
2. Langhoff, E. et al. (1991) Proc. Natl. Acad. Sci. USA 88, 7998–8002.
3. Lasky, L. A. et al. (1987) Cell 50, 975–985.
4. Sattentau, Q. J., and Moore, J. P. (1991) J.Exp.Med. 174, 407–415.
5. Maddon, P. J. et. al. (1988) Cell 54, 865–874.
6. Maddon, P. J. et al. (1988) PCT W088/01304.
7. Moore, J. P. et al. (1990) Science 250, 1139–1142.
8. Schooley, R. T. et al. (1990) Ann. Internal Med. 112, 247–253.
9. Kahn, J. O. et al. (1990) Ann. Internal Med. 112, 254–261.
10. Daar, E. S. et al. (1990) Proc. Natl. Acad. U.S.A. 87, 6574–6578.
11. Capon, D. J. et al. (1989) Nature 337, 525–531.
12. Byrn, R. A. et al. (1990) Nature 344, 667–670.
13. Ward, R. H. et al. (1991) Nature 352, 376–377.
14. Pound, J. D., and Walker, M. R. (1990) In: The Human IgG Subclasses, Ed. F.Shakib. Pergamon Press, Oxford, UK. pp.111–133.
15. Bolognesi, D. P. (1990) TIBTech 8, 40–45.
16. Skinner, M. A. et al. (1988) J. Virol. 62, 4195–4200.
17. Thall, M. et al. (1992) J. Virol. 66, 5635–5641.
18. Natuigepy H. et al. (1992) In: Proceedings of the 7th Colloque Des Cent Gardes, 299–303 Ed. O. Robert, L'Imprimerie Martineau, 69100 Villeurbanne, France.
19. Tilley, S. A., et al. (1992) AIDS Res. Hum. Retrovir. 8, 461–467.
20. Buchbinder et al. (1992) AIDS Res. Hum. Retrovir. 8, 425–427.
21. Thali, M. et al. (1992) J. AIDS 5, 591–599.
22. Dalgleish et al. (1984) Nature, 312, 763–767.
23. Chou, T-C. (1991) In: Synergism and Antagonism in Chemotherapy, Eds. Chou, T-C and Rideout, D.C. Academic Press, Inc. San Diego. pp. 61–102.
24. Durda P. J. et al. (1990) AIDS Res. Hum. Retrovir. 6, 1115–1123.
25. Remington's Pharmaceutical Science, 16th Ed., Mack Ed. (1990).

---

What is claimed is:

1. A composition comprising (a) a carrier;

(b) a CD4-immunoconjugate selected from the group consisting of a CD4-IgG2 chimeric heavy chain homodimer whose chains are encoded by the expression vector designated CD4-IgG2-pcDNA1 having ATCC Accession No. 40952, and a CD4-IgG2 heterotetramer comprising two chimeric heavy chains and two chimeric light chains, wherein the chimeric heavy chains of said heterotetramer are encoded by the expression vector designated CD4-IgG2HC-pRcCMV having ATCC Accession No. 75193 and the chimeric light chains of said heterotetramer are encoded by the expression vector designated CD4-kLC-pRcCMV having ATCC Accession No. 75194; and (c) an antibody which specifically binds to an epitope which is present on an HIV-1 envelope glycoprotein and which is required for the fusion of a CD4-containing membrane with a membrane containing the HIV-1 envelope glycoprotein; the molar ratio of antibodies to CD4-immunoconjugates being between 1:1.5 and 1:6.

2. The composition of claim 1, wherein the antibody is capable of forming a complex with an epitope present on HIV-1 gp120 envelope glycoprotein.

3. The composition of claim 2, wherein the antibody is capable of forming a complex with an epitope present on the V3 loop of HIV-1 gp120 envelope glycoprotein.

4. The composition of claim 1, wherein the antibody is capable of forming a complex with an epitope present on HIV-1 gp41 envelope glycoprotein.

5. The composition of claim 4, wherein the antibody is capable of forming a complex with an epitope present on HIV-1 gp41 envelope glycoprotein, said epitope comprising the amino acid sequence ELDKWA (SEQ ID NO:1).

6. The composition of claim 5, wherein the antibody is the monoclonal antibody designated 2F5.

* * * * *

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
        ( A ) LENGTH: 6 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:1:

Glu   Leu   Asp   Lys   Trp   Ala
    1                            5

( 2 ) INFORMATION FOR SEQ ID NO:2:

( i ) SEQUENCE CHARACTERISTICS:
        ( A ) LENGTH: 15 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:2:

-continued

| | | | | | | | | | | | | | | |
|---|---|---|---|---|---|---|---|---|---|---|---|---|---|---|
| Arg | Ile | Gln | Arg | Gly | Pro | Gly | Arg | Ala | Phe | Val | Thr | Ile | Gly | Lys |
| 1 | | | | 5 | | | | | 10 | | | | | 15 |